(12) United States Patent
Flick

(10) Patent No.: US 9,763,476 B2
(45) Date of Patent: Sep. 19, 2017

(54) AEROSOL GENERATING SYSTEM HAVING MEANS FOR HANDLING CONSUMPTION OF A LIQUID SUBTRATE

(75) Inventor: Jean-Marc Flick, Pomy (CH)

(73) Assignee: Philip Morris Products S.A., Neuchatel (CH)

( * ) Notice: Subject to any disclaimer, the term of this patent is extended or adjusted under 35 U.S.C. 154(b) by 942 days.

(21) Appl. No.: 13/996,725

(22) PCT Filed: Dec. 22, 2011

(86) PCT No.: PCT/EP2011/073795
§ 371 (c)(1),
(2), (4) Date: Aug. 20, 2013

(87) PCT Pub. No.: WO2012/085207
PCT Pub. Date: Jun. 28, 2012

(65) Prior Publication Data
US 2013/0319435 A1    Dec. 5, 2013

(30) Foreign Application Priority Data
Dec. 24, 2010 (EP) .................................. 10252234

(51) Int. Cl.
*A24F 47/00* (2006.01)
*A61M 15/06* (2006.01)
(Continued)

(52) U.S. Cl.
CPC .......... *A24F 47/008* (2013.01); *A61M 11/041* (2013.01); *A61M 11/042* (2014.02);
(Continued)

(58) Field of Classification Search
CPC ....... A61M 15/06; A24F 47/00; A24F 47/002; A24F 47/006
See application file for complete search history.

(56) References Cited

U.S. PATENT DOCUMENTS 2,057,353 A    10/1936 Whittemore, Jr.
5,062,145 A *  10/1991 Zwaan .................. A61M 16/16
                                                    392/395
(Continued)

FOREIGN PATENT DOCUMENTS

CN          1122213 A       5/1996
CN        100342753 C      10/2007
(Continued)

OTHER PUBLICATIONS

U.S. Appl. No. 13/996,716, filed Jun. 21, 2013, Cochand, et al.
(Continued)

*Primary Examiner* — Anthony Calandra
(74) *Attorney, Agent, or Firm* — Oblon, McClelland, Maier & Neustadt, L.L.P.

(57) ABSTRACT

There is provided an electrically operated aerosol generating system for receiving an aerosol-forming substrate. The system includes a liquid storage portion for storing liquid aerosol-forming substrate, an electric heater including at least one heating element for heating the liquid aerosol-forming substrate, and electric circuitry configured to monitor activation of the electric heater and estimate an amount of liquid aerosol-forming substrate remaining in the liquid storage portion based on the monitored activation. There is also provided a method in an electrically operated aerosol generating system including a liquid storage portion for storing liquid aerosol-forming substrate and an electric heater including at least one heating element for heating the liquid aerosol-forming substrate, the method including monitoring activation of the electric heater and estimating an amount of liquid aerosol-forming substrate remaining in the liquid storage portion based on the monitored activation.

11 Claims, 5 Drawing Sheets

(51) Int. Cl.
*A61M 11/04* (2006.01)
*A61M 15/00* (2006.01)
*A61M 16/00* (2006.01)

(52) U.S. Cl.
CPC .......... *A61M 15/008* (2014.02); *A61M 15/06* (2013.01); *A61M 2016/0021* (2013.01); *A61M 2205/3368* (2013.01); *A61M 2205/3389* (2013.01); *A61M 2205/3653* (2013.01); *A61M 2205/8206* (2013.01)

(56) References Cited

U.S. PATENT DOCUMENTS

| | | | |
|---|---|---|---|
| 5,743,251 | A | 4/1998 | Howell et al. |
| 2002/0079309 | A1 | 6/2002 | Cox et al. |
| 2004/0129793 | A1* | 7/2004 | Nguyen ............... A61M 11/041 239/13 |
| 2009/0283103 | A1 | 11/2009 | Nielsen et al. |
| 2010/0313901 | A1 | 12/2010 | Fernando et al. |
| 2011/0036346 | A1* | 2/2011 | Cohen ............... A61M 15/0065 128/200.14 |
| 2011/0278189 | A1* | 11/2011 | Terry .................... A24F 47/008 206/459.1 |
| 2012/0048266 | A1* | 3/2012 | Alelov ................ A61M 11/005 128/202.21 |

FOREIGN PATENT DOCUMENTS

| | | |
|---|---|---|
| EA | 201390961 A1 | 1/2014 |
| EP | 2 253 233 | 11/2010 |
| JP | 2003-290356 A | 10/2003 |
| JP | 2008-513071 A | 5/2008 |
| JP | 2009-119127 A | 6/2009 |
| WO | 2007 078273 | 7/2007 |

OTHER PUBLICATIONS

Extended European Search Report issued May 19, 2011, in European Patent Application No. 10252234.9.
International Search Report and Written Opinion issued Apr. 24, 2012, in PCT/EP2011/073795 filed Dec. 22, 2011.
Office Action issued Jul. 9, 2014 in Colombian Patent Application No. 13-171830-5 (submitting English translation only).
Combined Chinese Office Action and Search Report issued Oct. 28, 2015 in Patent Application No. 201180066544.2 (submitting English translation only).
Combined Chinese Office Action and Search Report issued Jun. 30, 2015 in Patent Application No. 201180066544.2 (submitting English translation only).
Combined Chinese Office Action and Search Report issued Jan. 4, 2016 in Patent Application No. 201180066544.2 (submitting English translation only).
Office Action issued Dec. 2, 2015 in Japanese Patent Application No. 2012-545409 (submitting English translation only).
International Search Report Issued Apr. 24, 2012 in PCT/EP11/73795 Filed Dec. 22, 2011.
Israeli Office Action issued on Aug. 14, 2016 in Patent Application No. 226909 (English translation only).
Eurasian Office Action issued on Aug. 1, 2016 in Patent Application No. 201390963/31 (English translation only).

* cited by examiner

AEROSOL GENERATING SYSTEM HAVING MEANS FOR HANDLING CONSUMPTION OF A LIQUID SUBTRATE

CROSS REFERENCE TO RELATED APPLICATION

This application is a national phase application based on PCT/EP2011/073795, filed on Dec. 22, 2011.

The present invention relates to an electrically operated aerosol generating system. In particular, the present invention relates to an electrically operated aerosol generating system in which the aerosol-forming substrate is liquid and is contained in a liquid storage portion.

WO 2007/078273 discloses an electric smoking utensil. A liquid is stored in a container which communicates with a heater vaporiser, powered by a battery supply, via a series of small apertures. The heater is in the form of a spirally wound electric heater mounted on an electrically insulating support. In use, the heater is activated by the mouth of a user to switch on the battery power supply. Suction on a mouthpiece by the user causes air to be drawn through holes in the container, over the heater vaporiser, into the mouthpiece and subsequently into the mouth of a user.

The electrically operated aerosol generating systems of the prior art, including the smoking system referred to above, do have a number of advantages, but there is still opportunity for improvement in the design, particularly concerning the handling of liquid aerosol-forming substrate stored in the container.

According to a first aspect of the invention, there is provided an electrically operated aerosol generating system for receiving an aerosol-forming substrate, the system comprising: a liquid storage portion for storing liquid aerosol-forming substrate; an electric heater comprising at least one heating element for heating the liquid aerosol-forming substrate; and electric circuitry configured to monitor activation of the electric heater and estimate an amount of liquid aerosol-forming substrate remaining in the liquid storage portion based on the monitored activation.

The aerosol generating system is arranged to vaporize the aerosol-forming substrate to form the aerosol. As known to those skilled in the art, an aerosol is a suspension of solid particles or liquid droplets in a gas, such as air.

Activation of the electric heater may be monitored in several ways, for example by monitoring the temperature of the heating element over time, the resistance of the heating element over time, or the power applied to the heater over time, or a combination of two or more of these parameters.

Preferably, the electric circuitry is configured to estimate a consumed amount of liquid aerosol-forming substrate, and to subtract the consumed amount from a known initial amount to provide an estimate of liquid aerosol-forming substrate remaining in the liquid storage portion.

Preferably, the electric circuitry is configured to monitor activation of the electric heater by monitoring the temperature or resistance of the heating element over time to estimate a consumed amount of aerosol-forming substrate. Preferably, the electric circuitry is configured to estimate a consumed amount of aerosol based on a first equation relating heating element temperature or resistance to aerosol-forming substrate consumption up to a first threshold of temperature or resistance and based on a second equation relating heating element temperature or resistance to aerosol-forming substrate consumption above the first threshold of temperature or resistance.

Preferably the second equation is a linear equation. Preferably, the second equation is dependent on power applied to the heating element. The second equation preferably accounts for thermal diffusion through the aerosol forming substrate and any element holding the aerosol forming substrate.

Preferably, the first equation is a non-linear equation. Preferably, the first equation is independent of power applied to the heating element. The first equation preferably accounts for the enthalpy of vaporisation of the liquid aerosol-forming substrate.

The value of the first threshold is dependent on the composition of the liquid aerosol forming substrate. Preferably, the first threshold is the boiling point of the liquid aerosol-forming substrate, and more preferably the boiling point of the liquid aerosol-forming substrate at atmospheric pressure.

The first equation and second equations are also dependent on the composition of the liquid aerosol-forming substrate, as well as the specific properties of the system, such as dimensions and material properties, and the power applied to the heater. The first and second equations are therefore preferably empirically derived and stored in the electric circuitry. A plurality of different equations may be stored in the electric circuitry for use with different compositions of liquid aerosol-forming substrate and for use at different power levels.

Of course, as an alternative to two equations to model the relationship between temperature or resistance and substrate consumption, a single more complex equation may be used, which is derived by correlation with empirically derived data for substrate consumption. Alternatively, three or more equations may be used if appropriate. But the inventors have appreciated that for an accurate calculation of liquid substrate consumption the temperature evolution of the heating element must be considered as well as the different evaporation behaviour above and below the boiling point of the liquid substrate. It is also desirable to provide different models for different power levels applied to the heater.

Providing electric circuitry for determining an amount of liquid aerosol-forming substrate in the liquid storage portion is advantageous for a number of reasons. For example, when the liquid storage portion is empty or nearly empty, insufficient liquid aerosol-forming substrate may be supplied to the electric heater. This may mean that the aerosol created does not have the desired properties, for example, aerosol particle size. This may result in a poor experience for the user. In addition, if it can be determined when the liquid storage portion is empty or nearly empty, it may be possible to inform the user. Then the user can prepare to replace or refill the liquid storage portion.

For the liquid aerosol-forming substrate, certain physical properties, for example the vapour pressure or viscosity of the substrate, are chosen in a way to be suitable for use in the aerosol generating system. The liquid preferably comprises a tobacco-containing material comprising volatile tobacco flavour compounds which are released from the liquid upon heating. Alternatively, or in addition, the liquid may comprise a non-tobacco material. The liquid may include water, ethanol, or other solvents, plant extracts, nicotine solutions, and natural or artificial flavours. Preferably, the liquid further comprises an aerosol former. Examples of suitable aerosol formers are glycerine and propylene glycol.

An advantage of providing a liquid storage portion is that the liquid in the liquid storage portion is protected from ambient air. In some embodiments, ambient light, cannot enter the liquid storage portion as well, so that the risk of degradation of the liquid is avoided. Moreover, a high level of hygiene can be maintained. If the liquid storage portion is not refillable and the liquid in the liquid storage portion has been used up or has decreased to a predetermined threshold, the liquid storage portion has to be replaced by the user. During such replacement, contamination of the user with the liquid has to be prevented. Alternatively, the liquid storage portion may be refillable. In that case, when the amount of liquid aerosol-forming substrate in the liquid storage portion has decreased to a predetermined threshold, the liquid storage portion may be refilled. Preferably, the liquid storage portion is arranged to hold liquid for a pre-determined number of puffs or heating cycles.

The electric heater may comprise a single heating element. Alternatively, the electric heater may comprise more than one heating elements for example two, or three, or four, or five, or six or more heating elements. The heating element or heating elements may be arranged appropriately so as to most effectively heat the liquid aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. The liquid storage portion may incorporate a disposable heating element. Alternatively, one or more heating needles or rods that run through the liquid aerosol-forming substrate may also be suitable. Alternatively, the at least one electric heating element may comprise a flexible sheet of material. Other alternatives include a heating wire or filament, for example a Ni—Cr (Nickel-Chromium), platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the liquid aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The at least one heating element may heat the liquid aerosol-forming substrate by means of conduction. The heating element may be at least partially in contact with the substrate. Alternatively, the heat from the heating element may be conducted to the substrate by means of a heat conductive element.

Alternatively, the at least one heating element may transfer heat to the incoming ambient air that is drawn through the electrically operated aerosol generating system during use, which in turn heats the aerosol-forming substrate. The ambient air may be heated before passing through the aerosol-forming substrate. Alternatively, the ambient air may be first drawn through the liquid substrate and then heated.

Preferably, the electrically operated aerosol generating system further comprises a capillary wick for conveying the liquid aerosol-forming substrate from the liquid storage portion to the electric heater.

Preferably, the capillary wick is arranged to be in contact with liquid in the liquid storage portion. Preferably, the capillary wick extends into the liquid storage portion. In that case, in use, liquid is transferred from the liquid storage portion to the electric heater by capillary action in the capillary wick. In one embodiment, the capillary wick has a first end and a second end, the first end extending into the liquid storage portion for contact with liquid therein and the electric heater being arranged to heat liquid in the second end. When the heater is activated, the liquid at the second end of the capillary wick is vaporized by the at least one heating element of the heater to form the supersaturated vapour. The supersaturated vapour is mixed with and carried in the air flow. During the flow, the vapour condenses to form the aerosol and the aerosol is carried towards the mouth of a user. The liquid aerosol-forming substrate has physical properties, including viscosity and surface tension, which allow the liquid to be transported through the capillary wick by capillary action.

The capillary wick may have a fibrous or spongy structure. The capillary wick preferably comprises a bundle of capillaries. For example, the capillary wick may comprise a plurality of fibres or threads or other fine bore tubes. The fibres or threads may be generally aligned in the longitudinal direction of the aerosol generating system. Alternatively, the capillary wick may comprise sponge-like or foam-like material formed into a rod shape. The rod shape may extend along the longitudinal direction of the aerosol generating system. The structure of the wick forms a plurality of small bores or tubes, through which the liquid can be transported by capillary action. The capillary wick may comprise any suitable material or combination of materials. Examples of suitable materials are capillary materials, for example a sponge or foam material, ceramic- or graphite-based materials in the form of fibres or sintered powders, foamed metal or plastics material, a fibrous material, for example made of spinned or extruded fibres, such as cellulose acetate, polyester, or bonded polyolefin, polyethylene, terylene or polypropylene fibres, nylon fibres or ceramic. The capillary wick may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

Preferably, the at least one heating element is in the form of a heating wire or filament encircling, and optionally supporting, the capillary wick. The capillary properties of the wick, combined with the properties of the liquid, ensure that, during normal use, the wick is always wet in the heating area. If the wick is dry, there may be overheating. Providing a capillary wick may therefore be advantageous as it will allow a measure of this overheating, which in turn can allow a determination of when the amount of liquid aerosol-forming substrate in the liquid storage portion has decreased to a predetermined threshold The capillary wick and the heater, and optionally the liquid storage portion, may be removable from the aerosol generating system as a single component.

In one case, the electric circuitry comprises a sensor to detect air flow indicative of a user taking a puff. In that case, preferably, the electric circuitry is arranged to provide an electric current pulse to the electric heater at a predetermined power when the sensor senses a user taking a puff. The time-period of the electric current pulse may be pre-set, depending on the amount of liquid desired to be vaporized. The electric circuitry is preferably programmable for this purpose. In that embodiment, the electric circuitry may be arranged to monitor the total time of the time-periods of the electric current pulses and from the monitored total time, predict when the amount of liquid aerosol-forming substrate in the liquid storage portion will decrease to the predetermined threshold.

The electrically operated aerosol generating system may further comprise a temperature sensor for measuring the temperature of the at least one heating element and the electric circuitry configured to monitor the temperature of the at least one heating element as sensed by the temperature sensor.

In another embodiment, the electric circuitry is arranged to measure the electrical resistance of the at least one heating element, to ascertain the temperature of the heating element from the measured electrical resistance.

In that embodiment, the electric circuitry may be arranged to measure the electrical resistance of the at least one heating element by measuring the current through the at least one heating element and the voltage across the at least one heating element and determining the electrical resistance of the at least one heating element from the measured current and voltage. In that case, the electric circuitry may comprise a resistor, having a known resistance, in series with the at least one heating element and the electric circuitry may be arranged to measure the current through the at least one heating element by measuring the voltage across the known resistance and determining the current through the at least one heating element from the measured voltage and the known resistance.

In an alternative case, the electric circuitry comprises a manually operable switch for a user to initiate a puff. The electric circuitry is arranged to provide an electric current pulse to the electric heater when the user initiates a puff. The time-period of the electric current pulse is preferably pre-set depending on the amount of liquid desired to be vaporized. The electric circuitry is preferably programmable for this purpose. In that embodiment, the electric circuitry may be arranged to monitor the total time in which the manually operable switch is activated and, from the monitored total time, estimate an amount of liquid aerosol-forming substrate in the liquid storage portion.

The electric circuitry may comprise a sensor for detecting the presence of a liquid storage portion. The sensor is preferably able to distinguish one liquid storage portion from another liquid storage portion and hence ascertain how much liquid aerosol-forming substrate is contained in the liquid storage portion when full. The sensor may also be able to determine the composition of the liquid in the liquid storage portion based on indicia on the liquid storage portion or the shape or size of the liquid storage portion. This, coupled with the monitored activation, may allow the electric circuitry to predict the amount of liquid aerosol-forming substrate in the liquid storage portion during use.

In a preferred embodiment, the electric circuitry is arranged, when the amount of liquid aerosol-forming substrate in the liquid storage portion has decreased to a predetermined threshold, to deactivate the electric heater.

This is advantageous because the user can then no longer use the aerosol generating system once there is insufficient liquid aerosol-forming substrate. This will avoid creation of an aerosol which does not have the desired properties. This will avoid a poor experience for the user.

The electric circuitry may be arranged to deactivate the electric heater by blowing an electrical fuse between the electric heater and an electric power supply. The electric circuitry may be arranged to deactivate the electric heater by switching off a switch between the electric heater and an electric power supply. Alternative methods of deactivating the electric heater will be apparent to the skilled person.

In a preferred embodiment, the electric circuitry is arranged, when the amount of liquid aerosol-forming substrate in the liquid storage portion has decreased to a predetermined threshold, to indicate this to a user. This is advantageous because the indication enables the user to refill or replace the liquid storage portion.

The electrically operated aerosol generating system may comprise a user display. In that case, the indication may comprise an indication on the user display. Alternatively, the indication may comprise an audible indication, or any other suitable type of indication for a user.

The aerosol generating system may further comprise an electric power supply. Preferably, the aerosol generating system comprises a housing. Preferably, the housing is elongate. If the aerosol generating includes a capillary wick, the longitudinal axis of the capillary wick and the longitudinal axis of the housing may be substantially parallel. The housing may comprise a shell and a mouthpiece. In that case, all the components may be contained in either the shell or the mouthpiece. In one embodiment, the housing includes a removable insert comprising the liquid storage portion, the capillary wick and the heater. In that embodiment, those parts of the aerosol generating system may be removable from the housing as a single component. This may be useful for refilling or replacing the liquid storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol generating system is portable. The aerosol generating system may be a smoking system and may have a size comparable to a conventional cigar or cigarette. The smoking system may have a total length between approximately 30 mm and approximately 150 mm. The smoking system may have an external diameter between approximately 5 mm and approximately 30 mm.

Preferably, the electrically operated aerosol generating system is an electrically heated smoking system.

According to a second aspect of the invention, there is provided a method comprising: providing an electrically operated aerosol generating system comprising a liquid storage portion for storing liquid aerosol-forming substrate and an electric heater comprising at least one heating element for heating the liquid aerosol-forming substrate; and monitoring activation of the electric heater and estimating an amount of liquid aerosol-forming substrate remaining in the liquid storage portion based on the monitored activation.

Preferably, the step of monitoring activation of the electric heater comprises monitoring the temperature or resistance of the heating element over time to estimate a consumed amount of aerosol-forming substrate. Preferably, the estimate of a consumed amount of aerosol is based on a first equation relating heating element temperature or resistance to aerosol-forming substrate consumption up to a first threshold of temperature or resistance and based on a second equation relating heating element temperature or resistance to aerosol-forming substrate consumption above the first threshold of temperature or resistance.

Preferably, the second equation is a linear equation. The second equation preferably accounts for thermal diffusion through the aerosol forming substrate or an element holding the aerosol forming substrate.

Preferably, the first equation is a non-linear equation. The first equation preferably accounts for the enthalpy of vaporisation of the liquid aerosol-forming substrate.

According to a third aspect of the invention, there is provided electric circuitry for an electrically operated aerosol generating system, the electric circuitry being arranged to perform the method of the second aspect of the invention.

According to a fourth aspect of the invention, there is provided a computer program which, when run on programmable electric circuitry for an electrically operated aerosol generating system, causes the programmable electric circuitry to perform the method of the second aspect of the invention.

According to a fifth aspect of the invention, there is provided a computer readable storage medium having stored thereon a computer program according to the fourth aspect of the invention.

Features described in relation to the aerosol generating system of the invention may also be applicable to the method of the invention. And, features described in relation to the method of the invention may also be applicable to the aerosol generating system of the invention.

The invention will be further described, by way of example only, with reference to the accompanying drawings, of which:

Figure 1:
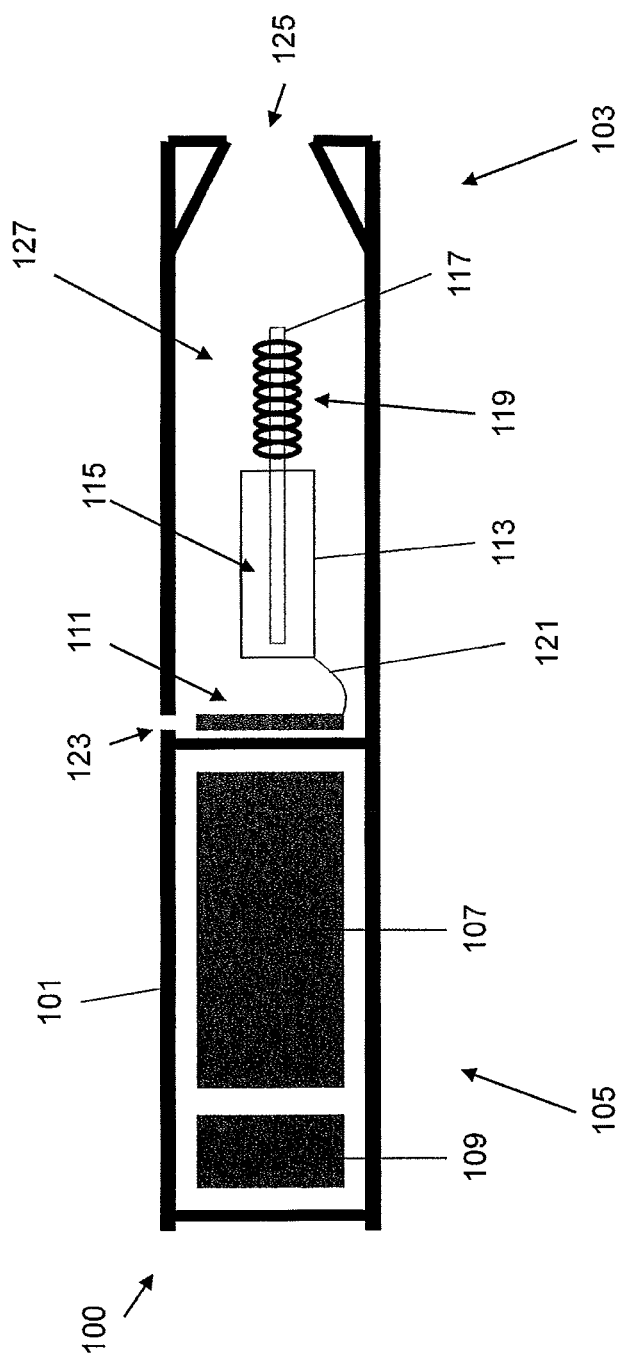
FIG. 1 shows one example of an electrically operated aerosol generating system having a liquid storage portion.
Figure 2:
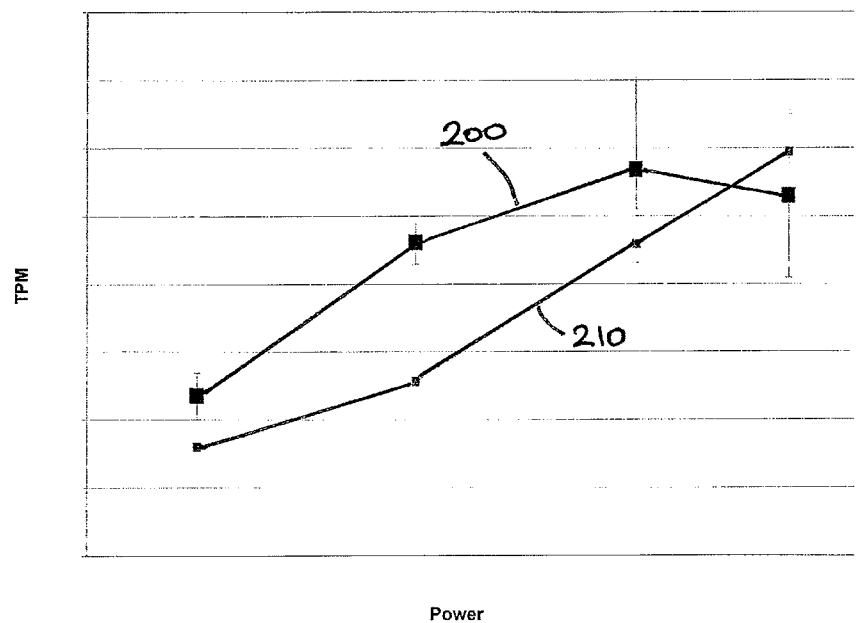
FIG. 2 is a plot of total particle mass versus power applied for two different liquid aerosol forming substrate compositions in a device of the type shown in FIG. 1.
Figure 3:
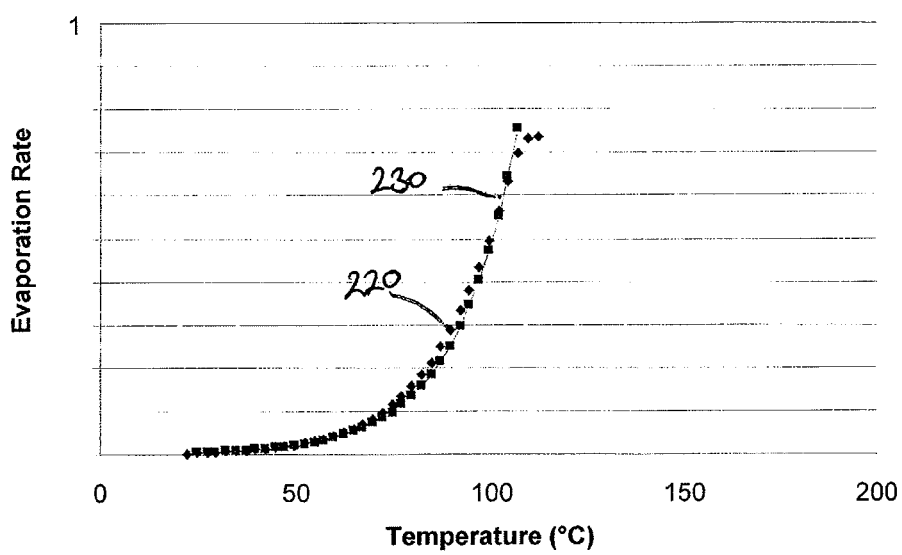
FIG. 3 is a plot of evaporation rate versus temperature of a liquid composition up to boiling point, together with a curve correlated to the plotted points.

FIG. 1 shows one example of an electrically operated aerosol generating system having a liquid storage portion. In FIG. 1, the system is a smoking system. The smoking system 100 of FIG. 1 comprises a housing 101 having a mouthpiece end 103 and a body end 105. In the body end, there is provided an electric power supply in the form of battery 107 and electric circuitry 109. A puff detection system 111 is also provided in cooperation with the electric circuitry 109. In the mouthpiece end, there is provided a liquid storage portion in the form of cartridge 113 containing liquid 115, a capillary wick 117 and a heater 119. Note that the heater is only shown schematically in FIG. 1. In the exemplary embodiment shown in FIG. 1, one end of capillary wick 117 extends into cartridge 113 and the other end of capillary wick 117 is surrounded by the heater 119. The heater is connected to the electric circuitry via connections 121, which may pass along the outside of cartridge 113 (not shown in FIG. 1). The housing 101 also includes an air inlet 123, an air outlet 125 at the mouthpiece end, and an aerosol-forming chamber 127.

In use, operation is as follows. Liquid 115 is conveyed by capillary action from the cartridge 113 from the end of the wick 117 which extends into the cartridge to the other end of the wick which is surrounded by heater 119. When a user draws on the aerosol generating system at the air outlet 125, ambient air is drawn through air inlet 123. In the arrangement shown in FIG. 1, the puff detection system 111 senses the puff and activates the heater 119. The battery 107 supplies electrical energy to the heater 119 to heat the end of the wick 117 surrounded by the heater. The liquid in that end of the wick 117 is vaporized by the heater 119 to create a supersaturated vapour. At the same time, the liquid being vaporized is replaced by further liquid moving along the wick 117 by capillary action. (This is sometimes referred to as "pumping action".) The supersaturated vapour created is mixed with and carried in the air flow from the air inlet 123. In the aerosol-forming chamber 127, the vapour condenses to form an inhalable aerosol, which is carried towards the outlet 125 and into the mouth of the user.

In the embodiment shown in FIG. 1, the electric circuitry 109 and puff detection system 111 are preferably programmable. The electric circuitry 109 and puff detection system 111 can be used to manage operation of the aerosol generating system. This assists with control of the particle size in the aerosol.

FIG. 1 shows one example of an electrically operated aerosol generating system according to the present invention. Many other examples are possible, however. In addition, note that FIG. 1 is schematic in nature. In particular, the components shown are not to scale either individually or relative to one another. The electrically operated aerosol generating system needs to include or receive a liquid aerosol-forming substrate contained in a liquid storage portion. The electrically operated aerosol generating system requires some sort of electric heater having at least one heating element for heating the liquid aerosol-forming substrate. Finally, the electrically operated aerosol generating system requires electric circuitry for determining an amount of liquid aerosol-forming substrate in the liquid storage portion. This will be described below with reference to FIGS. 2 to 9. It is emphasized that the system does not need to be a smoking system and a puff detection system does not need to be provided. Instead, the system could operate by manual activation, for example the user operating a switch when a puff is taken. For example, the overall shape and size of the housing could be altered. Moreover, the system may not include a capillary wick. In that case, the system may include another mechanism for delivering liquid for vaporization.

However, in a preferred embodiment, the system does include a capillary wick for conveying the liquid from the liquid storage portion to the at least one heating element. The capillary wick can be made from a variety of porous or capillary materials and preferably has a known, pre-defined capillarity. Examples include ceramic- or graphite-based materials in the form of fibres or sintered powders. Wicks of different porosities can be used to accommodate different liquid physical properties such as density, viscosity, surface tension and vapour pressure. The wick must be suitable so that the required amount of liquid can be delivered to the heater. Preferably, the heater comprises at least one heating wire or filament extending around the capillary wick.

As discussed above, according to the invention, the electrically operated aerosol generating system includes electric circuitry for determining an amount of liquid aerosol-forming substrate in the liquid storage portion. Embodiments of the invention will now be described with reference to FIGS. 2 to 9. The embodiments are based on the example shown in FIG. 1, although they are applicable to other embodiments of electrically operated aerosol generating systems.

FIG. 2 is a plot of the total particle mass (TPM) of aerosol generated in a user puff in a device as shown in FIG. 1, for two different aerosol forming substrates. Plot 200, with the plotted points drawn as larger squares, shows the results for Liquid 1 and plot 210, with the plotted points shown as smaller squares, shows the results for Liquid 2 The plots show the effect on aerosol generation of increasing power to the heater. It can be seen that increasing the power to the heater broadly increases aerosol generation. At very high power aerosol mass reduces, and this can be explained by the evaporated mass remaining in the gaseous phase rather than forming droplets.

FIG. 2 also illustrates that the mass of aerosol generated is also dependent on the composition of the liquid aerosol-forming substrate. For example, different compositions will have different boiling points and different viscosities. Any model to accurately estimate liquid aerosol-forming substrate consumption must therefore account for liquid composition and power applied to the heater.

The generation of aerosol requires supplying enough energy to the liquid to vaporise it. The energy required is called the enthalpy of vaporisation. The amount of energy supplied depends on the temperature of the heater element or elements: The higher the temperature the more energy is supplied to the liquid. So, up to the boiling point of the liquid, there is a relationship between the temperature of the heater elements and the evaporation rate. This is independent of the power supplied to the heater. FIG. 3 is a plot showing the evaporation rate of a liquid aerosol-forming substrate versus temperature up to its boiling point. The experimental data is plotted as diamonds 220. Also shown is a curve 230, drawn with square points, that is fitted to the experimental data 220. The curve 230 is of the form $m=Ae^{BT}$, where m is the evaporated mass rate, A and B are calibration constants and T is the temperature of the heating element. The constants A and B depend on the liquid composition.

Once the temperature of the heating element reaches the boiling point of the liquid the rate of evaporation no longer increases in the same manner. At this point further energy from the heating element does not increase the temperature of the liquid. However, as the temperature of the heating element increases beyond the boiling point thermal diffusion through the liquid substrate and more particularly through any medium holding the substrate, in this embodiment the capillary wick, becomes a significant factor. As the heating element temperature rises there is a greater rate of thermal diffusion so more liquid substrate is vaporised.

FIG. 4 is a plot of two different evaporation rate curves as a function of temperature using a wick system as shown in FIG. 1. The two curves 240 and 250 correspond to two different amounts of power supplied to the heating element during a puff. In both curves 240 and 250, the first portion below the boiling point of the liquid corresponds to the curve 230 shown in FIG. 3. Above the boiling point the two curves diverge. Curve 240, corresponds to a lower power than curve 250. Both curves show a linear increase in evaporation rate with temperature, but the rate of increase is clearly dependent on power. The portion of curves 240 and 250 above the boiling point of the liquid substrate are of the form $m=CT+D$, where m is the rate of evaporation, C and D are calibration constants and T is temperature. Constants C and D are dependent on liquid composition, the power applied to the heater as well as the physical properties of the device, such as the composition and dimensions of the wick and the configuration of the heater.

The curves of FIG. 4 provide a model that can be used to calculate the evaporation rate of the liquid substrate if the temperature of the heating element and the power applied to the heating element are known. For each design of aerosol generating system the constants A, B, C and D need to be empirically derived and constants C and D must be derived for the different power levels that the system can operate at.

The temperature of the heating element changes during the course of each puff and changes as the amount of liquid in the liquid storage portion is reduced. FIG. 5 is a plot showing five averaged temperature profiles during a puff. The temperature, T of the heating element is shown on the y-axis and the puff time t is shown on the x-axis. Curve 501 is the median of a first set of puffs, each puff having a 2-second puff duration. Similarly, curve 503 is the median of a second set of puffs, curve 505 is the median of a third set of puffs curve 507 is the median of a fourth set of puffs and curve 509 is the median over a fifth set of puffs. In each curve, the vertical bars (for example shown at 511) indicate the standard deviation around the median for those puffs. Thus, the evolution of the measured temperature over the life of the liquid storage portion is shown. This behaviour was observed and confirmed for all liquid formulations vaporized and for all power levels used.

Figure 4:
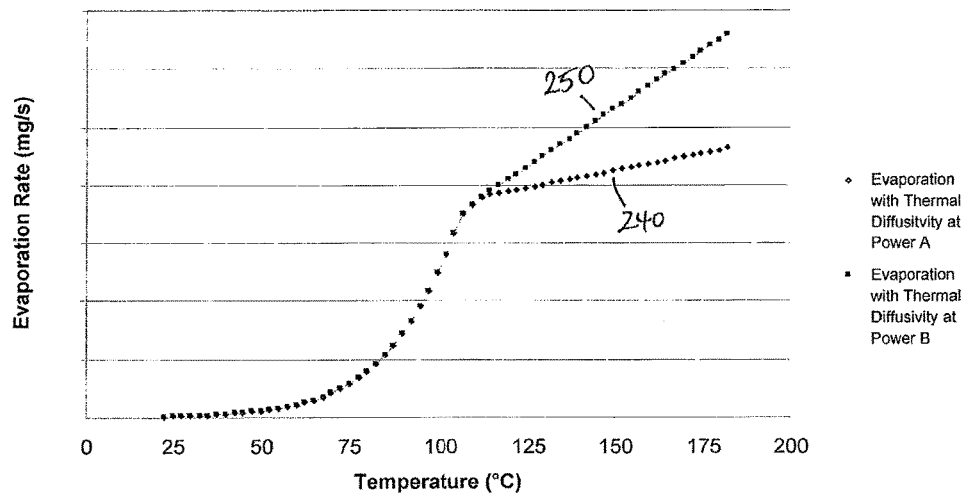
FIG. 4 is a plot showing the evaporation rate of a liquid composition versus temperature in a device of the type shown in FIG. 1, showing evaporation rate for two different power levels.
Figure 5:
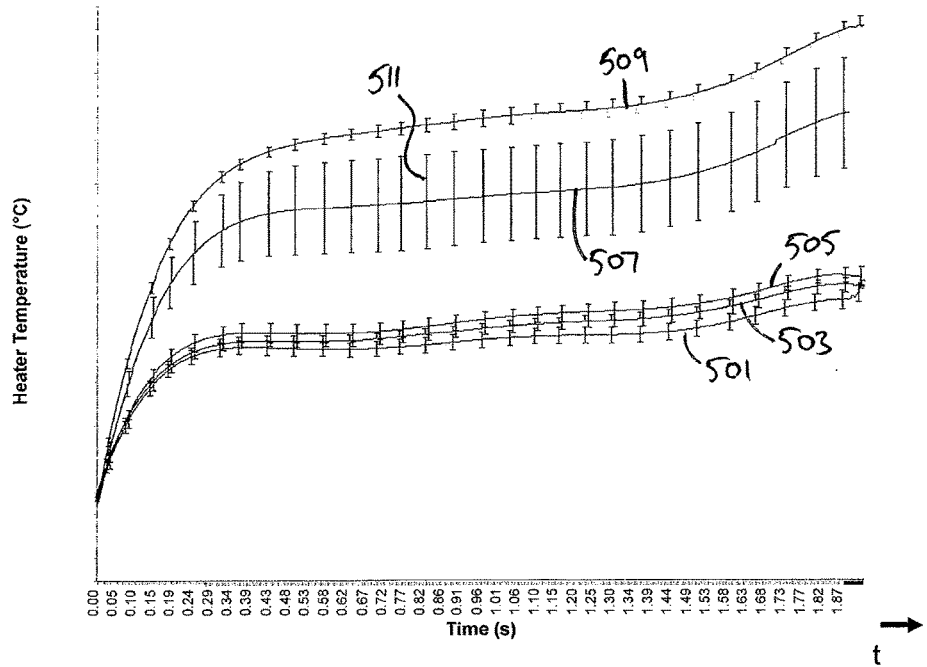
FIG. 5 is a plot showing the evolution of temperature of a heating element during a puff, with different plots shown for different stages in the consumption of the liquid aerosol forming substrate.

As can be seen from FIG. 5, the temperature response of the heating element is reasonably stable over curves 501, 503 and 205. That is to say, the standard deviation around the median for the first three sets of puffs is reasonably small. The model illustrated in FIG. 4 is most accurate during this period when the temperature response is stable. During this period there is always sufficient aerosol-forming substrate being delivered to the heater through the wick. Once the wick begins to dry a different behaviour is observed.

Figure 6:
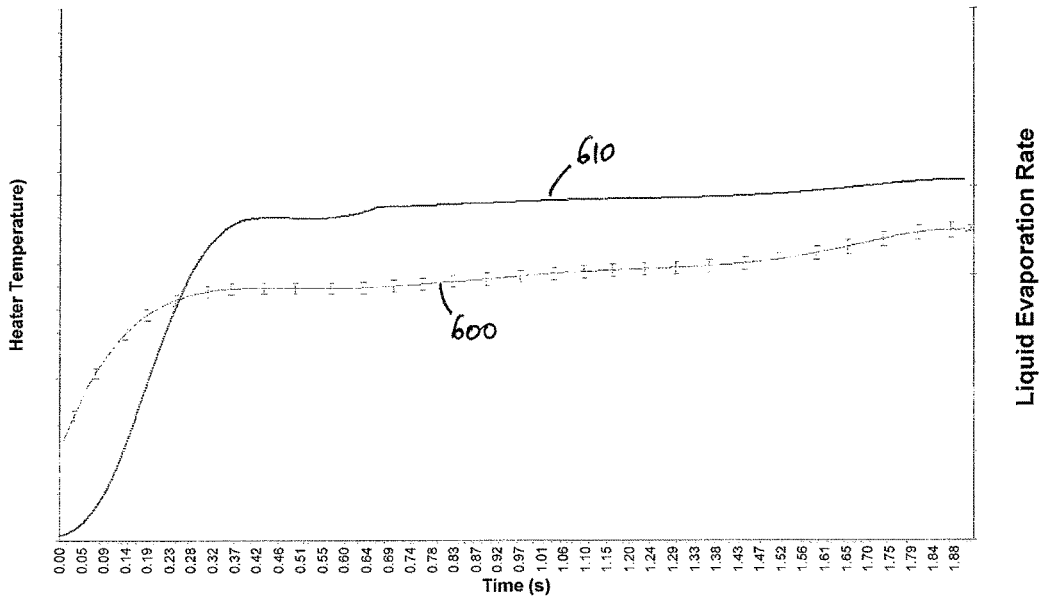
FIG. 6 is a plot showing the liquid evaporation rate during a puff and the corresponding temperature of the heating element.

FIG. 6 is an illustration of the temperature profile of a heating element during a puff (averaged over a set of puffs), shown as curve 600 together with the corresponding evaporation rate calculated using the model shown and described with reference to FIG. 4, shown as curve 610.

Figure 7:
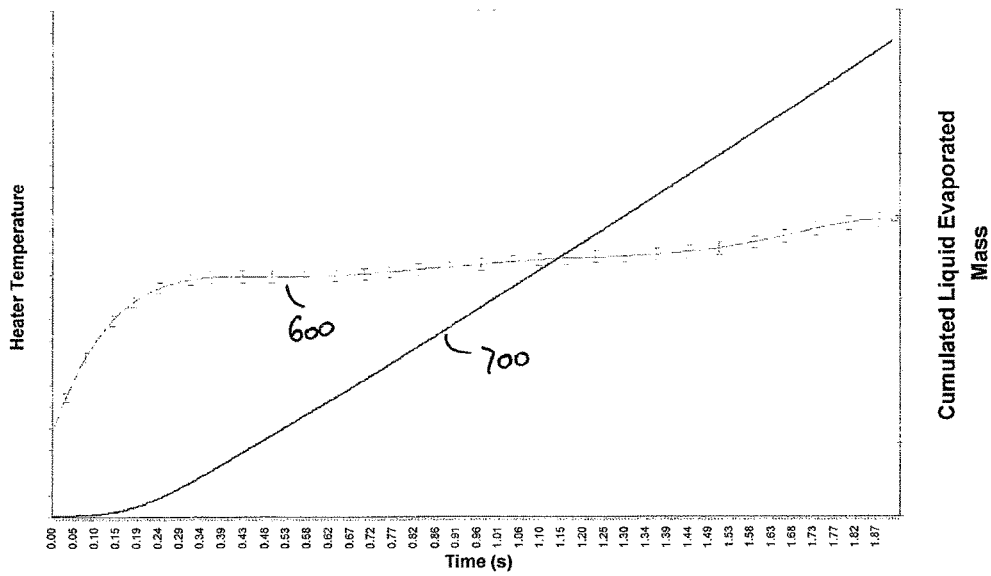
FIG. 7 is a plot showing the cumulative evaporated mass for a puff.

The total mass of liquid aerosol-forming substrate evaporated during a puff can be calculated by integrating under the evaporation rate curve 610. This integral can be performed by the electric circuitry using the trapezium method for example. The result of the integral is shown in FIG. 7. FIG. 7 again shows the temperature profile 600 of a heating element during a puff but also shows the cumulative evaporated mass over the puff as curve 700.

The total amount of liquid aerosol-forming substrate consumed can be calculated by summing the totals calculated for each puff. This total consumed mass can be subtracted from a known initial mass of liquid in the liquid storage portion to provide an estimate of the amount of liquid aerosol-forming substrate remaining. The amount remaining can be indicated to the user as a meaningful quantity, such as an estimated number of puffs remaining or as a percentage value.

Determining the amount of liquid aerosol-forming substrate in the liquid storage portion is advantageous because, when the liquid storage portion is empty or nearly empty, insufficient liquid aerosol-forming substrate may be supplied to the heater. This may mean that the aerosol created and inhaled by the user does not have the desired properties, for example, aerosol particle size. This may result in a poor experience for the user. In addition, it is advantageous to provide a mechanism whereby the user can be informed that the liquid storage portion is empty or nearly empty. Then the user can prepare to replace or refill the liquid storage portion.

The electric circuitry may include a sensor which is able to detect the presence of a liquid storage portion and, moreover, to determine the characteristics of the liquid storage portion including, for example, how much liquid aerosol-forming substrate is contained in the liquid storage portion and the composition of the liquid aerosol-forming substrate. As described in the applicant's pending International application PCT/IB2009/007969, this may be based on identification information provided on the liquid storage portion. This information, together with information derived from monitoring activation of the heater, allows the electric circuitry to predict the amount of liquid aerosol-forming substrate in the liquid storage portion. Alternatively, the electric circuitry does not need to include a sensor. For example, the amount of liquid aerosol-forming substrate in each liquid storage portion may simply be of only one kind and set at a standard amount.

A number of variations of the invention are possible. For example, the aerosol generating system does not need to include a puff detection system. Instead, the system could operate by manual activation, for example the user operating a switch when a puff is taken.

According to the first embodiment of the invention, a temperature sensor is provided in the aerosol generating system close to the heating element. The electric circuitry can monitor the temperature measured by the temperature sensor and hence determine an amount of liquid in the liquid storage portion as described. The advantage of this embodiment is that no calculation or derivation is required, since the temperature sensor directly measures the temperature close to the heating element.

According to the second embodiment of the invention, the amount of liquid in the liquid storage portion is determined by measuring the resistance of the electric heating element. If the heating element has suitable temperature coefficient of resistance characteristics (for example, see equation (5) below), then the resistance may provide a measure of the temperature of the electric heating element.

Figure 8:
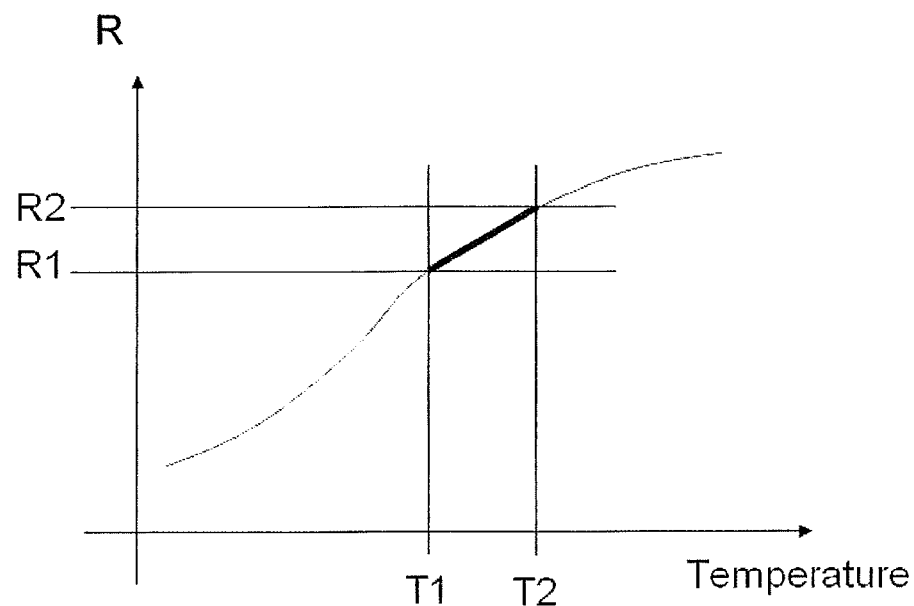
FIG. 8 is a plot showing, on the y-axis, heating element resistance and, on the x-axis, heating element temperature of an electric heater of an electrically operated aerosol generating system.

FIG. 8 is a plot showing the resistance, R of the heating element of the electric heater on the y-axis, versus the temperature, T of the heating element on the x-axis. As can be seen in FIG. 8, as the temperature T of the heating element increases, so does the resistance R. Within a selected range (between temperatures T1 and T2 and resistances R1 and R2 in FIG. 4), the temperature T and resistance R may be proportional to one another.

As discussed above in relation to the first embodiment of the invention, if the liquid storage portion is empty or nearly empty, insufficient liquid aerosol-forming substrate will be supplied to the heater. This will mean that any capillary wick will become dry, and the temperature of the heating element will increase. FIG. 8 shows that such a temperature increase may be determined by measuring the resistance of the heating element because, as the temperature increases, the measured resistance will increase as well.

Figure 9:
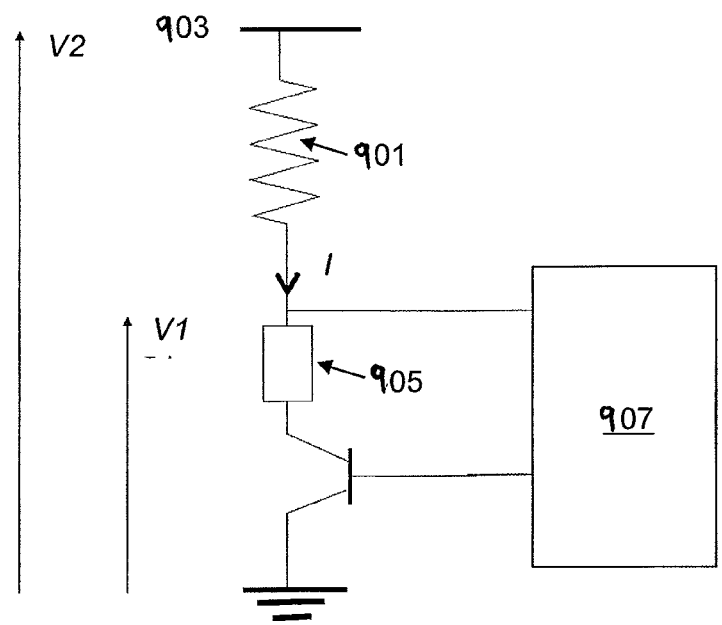
FIG. 9 is a schematic circuit diagram, which allows heating element resistance to be measured, according to one embodiment of the invention.

FIG. 9 is a schematic electric circuit diagram showing how the heating element resistance may be measured according to the second embodiment of the invention. In FIG. 9, the heater 901 is connected to a battery 903 which provides a voltage V2. The heater resistance to be measured at a particular temperature is $R_{heater}$. In series with the heater 901, an additional resistor 905, with known resistance r is inserted and connected to voltage V1. The voltage V1 has an intermediate value between ground and voltage V2. In order for microprocessor 907 to measure the resistance $R_{heater}$ of the heater 901, the current through the heater 901 and the voltage across the heater 901 can both be determined. Then, the following well-known formula can be used to determine the resistance:

$$V = IR \quad (1)$$

In FIG. 9, the voltage across the heater is V2−V1 and the current through the heater is I. Thus:

$$R_{heater} = \frac{V2 - V1}{I} \quad (2)$$

The additional resistor 905, whose resistance r is known, is used to determine the current I, again using (1) above. The current through the resistor 905 is I and the voltage across the resistor 905 is V1. Thus:

$$I = \frac{V1}{r} \quad (3)$$

So, combining (2) and (3) gives:

$$R_{heater} = \frac{(V2 - V1)}{V1}r \quad (4)$$

Thus, the microprocessor 907 can measure V2 and V1, as the aerosol generating system is being used and, knowing the value of r, can determine the heater's resistance at a particular temperature, $R_{heater}$.

Then, the following formula can be used to determine the temperature T from the measured resistance $R_{heater}$ at temperature T:

$$T = \frac{R_{heater}}{\alpha R_0} + T_0 - \frac{1}{\alpha} \quad (5)$$

where α is the thermal resistivity coefficient of the heating element material and $R_0$ is the resistance of the heating element at room temperature $T_0$.

An advantage of this embodiment is that no temperature sensor, which can be bulky and expensive, is required.

Thus, a measure of the temperature of the heating element can be derived. This can be used to determine when the amount of liquid in the liquid storage portion has decreased to a threshold and to estimate an absolute amount of aerosol-forming substrate remaining in the liquid storage portion.

In the embodiments described above, once it has been determined when the amount of liquid aerosol-forming substrate in the liquid storage portion has decreased to a threshold, one or more actions may be taken. The electric heater may be deactivated. For example, a system may be triggered to render the liquid storage portion unusable. For example, the electric circuitry, on determining that the amount of liquid aerosol-forming substrate in the liquid storage portion, has decreased to a threshold, may blow an electrical fuse between the at least one heating element of the electric heater and an electric power supply. The electrical fuse may be provided as part of a removable component including the liquid storage portion. Alternatively, the electric circuitry, on determining that the amount of liquid aerosol-forming substrate in the liquid storage portion, has decreased to a threshold, may switch off a switch between the at least one heating element of the electric heater and an electric power supply. Alternative methods of deactivating the electric heater are, of course, possible. An advantage of deactivating the electric heater is that it is then impossible to use the aerosol generating system. This renders it impossible for a user to inhale an aerosol which does not have the desired properties.

Once it has been determined when the amount of liquid in the liquid storage portion has decreased to a threshold, the user may be advised. For example, the electric circuitry, on determining that the amount of liquid aerosol-forming substrate in the liquid storage portion, has decreased to a threshold, may indicate this to a user. For example, if the aerosol generating system includes a user display, it may be indicated to the user, via the user display, that the liquid storage portion is empty or nearly empty. Alternatively or additionally, an audible sound may indicate to the user that the liquid storage portion is empty or nearly empty. Alternative methods of indicating to the user that the liquid storage portion is empty or nearly empty are, of course, possible. An advantage of advising the user is that the user is then able to prepare to replace or refill the liquid storage portion.

Thus, according to the invention, the electrically operated aerosol generating system includes electric circuitry for determining when the amount of liquid aerosol-forming substrate in the liquid storage portion has decreased to a predetermined threshold. Features described in relation to one embodiment may also be applicable to another embodiment.

The invention claimed is:

1. An electrically operated aerosol generating system configured to receive an aerosol-forming substrate, the system comprising:
    a liquid storage portion configured to store a liquid aerosol-forming substrate;
    an electric heater comprising at least one heating element configured to heat the liquid aerosol-forming substrate; and
    electric circuitry configured to
       monitor activation of the electric heater,
       estimate an amount of the liquid aerosol-forming substrate remaining in the liquid storage portion based on the monitored activation, and
       estimate a consumed amount of the liquid aerosol-forming substrate based on a first equation relating heating element temperature or resistance to liquid aerosol-forming substrate consumption up to a first threshold of temperature or resistance, and based on a second equation relating heating element temperature or resistance to liquid aerosol-forming substrate consumption above the first threshold.

2. The electrically operated aerosol generating system according to claim 1, wherein the electric circuitry is further configured to estimate a consumed amount of the liquid aerosol-forming substrate, and to subtract the consumed amount from a known initial amount to provide an estimate of an amount of the liquid aerosol-forming substrate remaining in the liquid storage portion.

3. The electrically operated aerosol generating system according to claim 1, wherein the electric circuitry is further configured to monitor activation of the electric heater by monitoring a temperature or a resistance of the at least one heating element over time.

4. The electrically operated aerosol generating system according to claim 1, wherein the second equation is dependent on power applied to the at least one heating element.

5. The electrically operated aerosol generating system according to claim 1, wherein the first equation is independent of power applied to the at least one heating element.

6. The electrically operated aerosol generating system according to claim 1, wherein the first threshold is a boiling point of the liquid aerosol-forming substrate.

7. The electrically operated aerosol generating system according to claim 1, wherein the first and second equations are stored in the electric circuitry.

8. The electrically operated aerosol generating system according to claim 7, wherein a plurality of different first and second equations are stored in the electric circuitry for different compositions of liquid aerosol-forming substrate and for different power levels.

9. The electrically operated aerosol generating system according to claim 1, wherein the electric circuitry is further configured to measure an electrical resistance of the at least one heating element, and to ascertain a temperature of the at least one heating element from a measured electrical resistance.

10. The electrically operated aerosol generating system according to claim 1, further comprising a capillary wick configured to convey the liquid aerosol-forming substrate from the liquid storage portion to the electric heater.

11. A method, comprising:
providing an electrically operated aerosol generating system comprising a liquid storage portion configured to store a liquid aerosol-forming substrate and an electric heater comprising at least one heating element configured to heat the liquid aerosol-forming substrate;
monitoring, by electric circuitry, activation of the electric heater and estimating, by the electric circuitry, an amount of the liquid aerosol-forming substrate remaining in the liquid storage portion based on the monitored activation; and
estimating, by the electric circuitry, a consumed amount of the liquid aerosol-forming substrate based on a first equation relating heating element temperature or resistance to liquid aerosol-forming substrate consumption up to a first threshold of temperature or resistance, and based on a second equation relating heating element temperature or resistance to liquid aerosol-forming substrate consumption above the first threshold.

* * * * *